United States Patent
Shen et al.

(10) Patent No.: US 11,013,398 B2
(45) Date of Patent: May 25, 2021

(54) SYSTEM FOR OBTAINING CLEAR ENDOSCOPE IMAGES

(71) Applicant: Stryker Corporation, Kalamazoo, MI (US)

(72) Inventors: John T. Shen, San Jose, CA (US); Benjamin H. Feingold, Tucson, AZ (US); Vasudev Nambakam, San Jose, CA (US); Amit A. Mahadik, San Jose, CA (US); Brandon B. Hunter, Hollister, CA (US)

(73) Assignee: Stryker Corporation, Kalamazoo, MI (US)

( * ) Notice: Subject to any disclaimer, the term of this patent is extended or adjusted under 35 U.S.C. 154(b) by 2051 days.

(21) Appl. No.: 14/159,003

(22) Filed: Jan. 20, 2014

(65) Prior Publication Data

US 2014/0275764 A1    Sep. 18, 2014

Related U.S. Application Data (60) Provisional application No. 61/779,693, filed on Mar. 13, 2013.

(51) Int. Cl.
*A61B 1/06*   (2006.01)
*A61B 1/00*   (2006.01)
*A61B 1/045*  (2006.01)

(52) U.S. Cl.
CPC ........ *A61B 1/0661* (2013.01); *A61B 1/00006* (2013.01); *A61B 1/00009* (2013.01); *A61B 1/045* (2013.01)

(58) Field of Classification Search
CPC ... A61B 1/00006; A61B 1/00009; A61B 1/04; A61B 1/041; A61B 1/045; A61B 1/06661; A61B 5/00; A61B 5/0084; A61B 5/6861; A61B 5/065; A61B 5/067; A61B 5/068; A61B 5/7425; G02B 23/00; G02B 23/24; H04N 5/232–247
USPC ....... 600/103, 109, 118, 160, 173, 176, 178, 600/180; 348/65, 68, 77; 362/551–552, 362/574
See application file for complete search history.

(56) References Cited

U.S. PATENT DOCUMENTS

| | | | |
|---|---|---|---|
| 6,836,288 B1 * | 12/2004 | Lewis | H04N 5/2352 348/221.1 |
| 6,879,731 B2 | 4/2005 | Kang et al. | |
| 7,010,174 B2 | 3/2006 | Kang et al. | |

(Continued)

*Primary Examiner* — Timothy J Neal
*Assistant Examiner* — William B Chou
(74) *Attorney, Agent, or Firm* — Morrison & Foerster LLP (57) ABSTRACT

An endoscopic system including an endoscope, a light source for the endoscope and at least one image sensor for capturing a plurality of images of a body cavity. The light source is configured to emit light from the endoscope and into the body cavity such that the light is reflected off of a plurality of locations in the body cavity. The system also includes a control system for controlling both the light source and the at least one image sensor to vary parameters of the light source and the at least one image sensor such that the plurality of images have underexposed and overexposed regions. The endoscopic system could alternatively include a variable-attenuator element device adjacent the image sensor and configured to be located between the body cavity and the image sensor for capturing a single clear image with the image sensor.

24 Claims, 9 Drawing Sheets

(56) References Cited

U.S. PATENT DOCUMENTS

| | | | |
|---|---|---|---|
| 7,239,757 B2 | 7/2007 | Kang et al. | |
| 7,454,136 B2 | 11/2008 | Raskar et al. | |
| 8,514,278 B2* | 8/2013 | Karpen | A61B 1/00036 348/69 |
| 8,891,087 B2* | 11/2014 | Zuzak | G01N 21/31 356/445 |
| 2003/0076412 A1* | 4/2003 | Ozawa | H04N 9/735 348/65 |
| 2003/0117491 A1* | 6/2003 | Avni | A61B 1/041 348/77 |
| 2005/0213092 A1* | 9/2005 | MacKinnon | G01J 1/32 356/336 |
| 2005/0228231 A1* | 10/2005 | MacKinnon | A61B 1/05 600/180 |
| 2005/0234302 A1* | 10/2005 | MacKinnon | A61B 1/00186 600/181 |
| 2006/0036131 A1* | 2/2006 | Glukhovsky | A61B 1/00186 600/160 |
| 2007/0225560 A1* | 9/2007 | Avni | A61B 1/00006 600/118 |
| 2008/0071144 A1* | 3/2008 | Fein | A61B 1/00167 600/178 |
| 2008/0180749 A1* | 7/2008 | Pollard | G06T 5/50 358/3.24 |
| 2008/0187235 A1* | 8/2008 | Wakazono | H04N 5/243 382/255 |
| 2008/0239070 A1* | 10/2008 | Westwick | A61B 1/045 348/68 |
| 2009/0040364 A1* | 2/2009 | Rubner | G06T 3/4053 348/362 |
| 2009/0076368 A1* | 3/2009 | Balas | A61B 1/00149 600/407 |
| 2009/0175555 A1* | 7/2009 | Mahowald | H04N 5/23232 382/274 |
| 2009/0225333 A1* | 9/2009 | Bendall | G01N 21/954 356/626 |
| 2009/0322865 A1* | 12/2009 | Wang | A61B 1/00009 348/68 |
| 2010/0016662 A1* | 1/2010 | Salsman | A61B 1/00096 600/109 |
| 2010/0220179 A1* | 9/2010 | Wang | A61B 1/00009 348/68 |
| 2010/0245552 A1* | 9/2010 | Higuchi | A61B 1/00096 348/68 |
| 2011/0109750 A1* | 5/2011 | Du | G01S 7/4814 348/180 |
| 2011/0122301 A1* | 5/2011 | Yamura | H04N 5/2256 348/262 |
| 2011/0208004 A1* | 8/2011 | Feingold | A61B 1/045 600/178 |
| 2012/0002394 A1* | 1/2012 | Todd | A61B 1/0653 362/13 |
| 2012/0008005 A1* | 1/2012 | Fukunishi | G06T 5/50 348/222.1 |
| 2012/0061590 A1* | 3/2012 | Khojasteh | G02B 21/367 250/459.1 |
| 2012/0197080 A1* | 8/2012 | Murayama | A61B 1/045 600/109 |
| 2012/0205519 A1* | 8/2012 | Mohler | G01J 1/20 250/206 |
| 2012/0274822 A1* | 11/2012 | Smith | H04N 5/23254 348/302 |
| 2013/0021447 A1* | 1/2013 | Brisedoux | H04N 5/2258 348/47 |
| 2014/0052004 A1* | 2/2014 | D'Alfonso | A61B 1/0669 600/476 |
| 2014/0063229 A1* | 3/2014 | Olsson | H04N 5/2252 348/84 |
| 2014/0160260 A1* | 6/2014 | Blanquart | H04N 5/35554 348/68 |
| 2014/0267825 A1* | 9/2014 | Ono | G02B 23/2461 348/222.1 |
| 2015/0327765 A1* | 11/2015 | Crane | A61B 5/0059 348/77 |

\* cited by examiner

SYSTEM FOR OBTAINING CLEAR ENDOSCOPE IMAGES

CROSS REFERENCE TO RELATED APPLICATION

This application claims the benefit of U.S. Provisional Application Ser. No. 61/779,693, filed Mar. 13, 2013, which is incorporated herein by reference in its entirety.

FIELD OF THE INVENTION

The present invention relates to a system for viewing clear images taken from an endoscope.

BACKGROUND OF THE INVENTION

An endoscope is a surgical tool designed to be placed inside a body in order to provide a view of the interior portion of the body. In endoscopic surgery, the endoscope is placed in the body at the location at which it is necessary to perform a surgical procedure. Other surgical instruments are placed in the body at the surgical site. The surgeon views the surgical site through the endoscope in order to manipulate the other surgical instruments to perform the desired surgical procedure. The development of endoscopes and their companion surgical instruments has made it possible to perform minimally invasive surgery that eliminates the need to make a large incision in the patient to gain access to the surgical site. Instead, during endoscopic surgery, small openings, called portals, are formed. One advantage of performing endoscopic surgery is that since the portions of the body that are cut are reduced, the portions of the body that need to heal after the surgery are likewise reduced. Still another advantage of endoscopic surgery is that it exposes less of the interior tissue of the patient's body to the open environment. This minimal opening of the patient's body lessens the extent to which the patient's internal tissue and organs are open to infection.

During endoscopic surgery, the environment of the body cavity may pose problems relating to proper operation of the endoscope. For example, a problem with images taken from within the body cavity is that portions of the body cavity can be either underexposed or overexposed depending on many factors including light intensities, exposure lengths and aperture sizes. The underexposed regions and overexposed regions of the images can obscure important features which would be desirable to distinguish.

BRIEF DESCRIPTION OF THE DRAWINGS

One or more embodiments of the present invention are illustrated by way of example and should not be construed as being limited to the specific embodiments depicted in the accompanying drawings, in which like reference numerals indicate similar elements.

DETAILED DESCRIPTION

Figure 1:
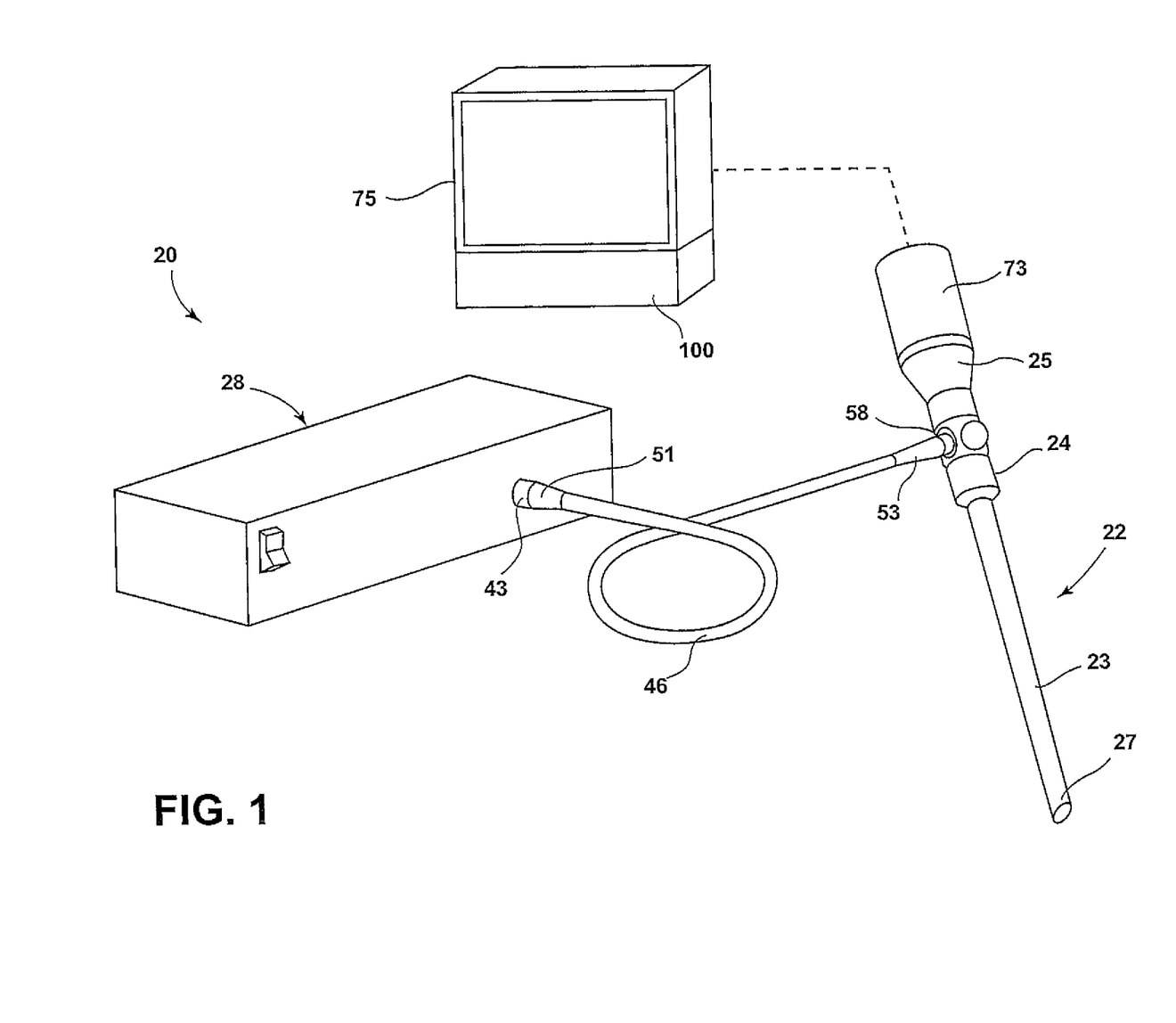
FIG. 1 illustrates a perspective schematic view of an endoscopic system according to the invention.

FIG. 1 illustrates an endoscopic system 20 including an endoscope 22, a transmission cable 46, and a light source console 28. The endoscope 22 is defined by an elongated and generally hollow shaft 23 with a distal end 27 configured for insertion within a body cavity. The hollow shaft 23 also has a proximal end 24 which mounts thereon an eyepiece 25 fitted to provide a viewing port through which the surgeon views the surgical field through a connection between the viewing port, a digital camera 73, and a display screen 75 of a computer 100 (e.g., a person computer or other viewing system). A light port 58 may be connected with light inputs to selectively transmit light to a target 50 (see FIG. 2) via the endoscope 22. In the illustrated embodiment, the light source console 28 sends electromagnetic waves to the distal end 27 of the endoscope 22 to heat the same to prevent fogging.

The light source console 28 selectively provides electromagnetic radiation as image capture light for use in the operating theater for illuminating the surgical field. In the present embodiment, the candlepower of the image capture light emitted from the light source console 28 is selectively adjustable. Further, the light source console 28 comprises a socket 43 to transmit the electromagnetic radiation from the light source console 28 to the endoscope 22 via intermediary devices, such as the transmission cable 46.

The illustrated transmission cable 46 is configured to transmit light from a proximal end 51 of the transmission cable 46 to a distal end 53 of the transmission cable 46 attached to the light port 58. The transmission cable 46 can comprise an optical fiber or optical fibers suited to transmit electromagnetic radiation via total internal reflection of such radiation within the fiber material. The proximal end 51 and the distal end 53 include terminal geometries, such as plugs, conducive to receiving and emitting, respectively, electromagnetic radiation.

Figure 2:
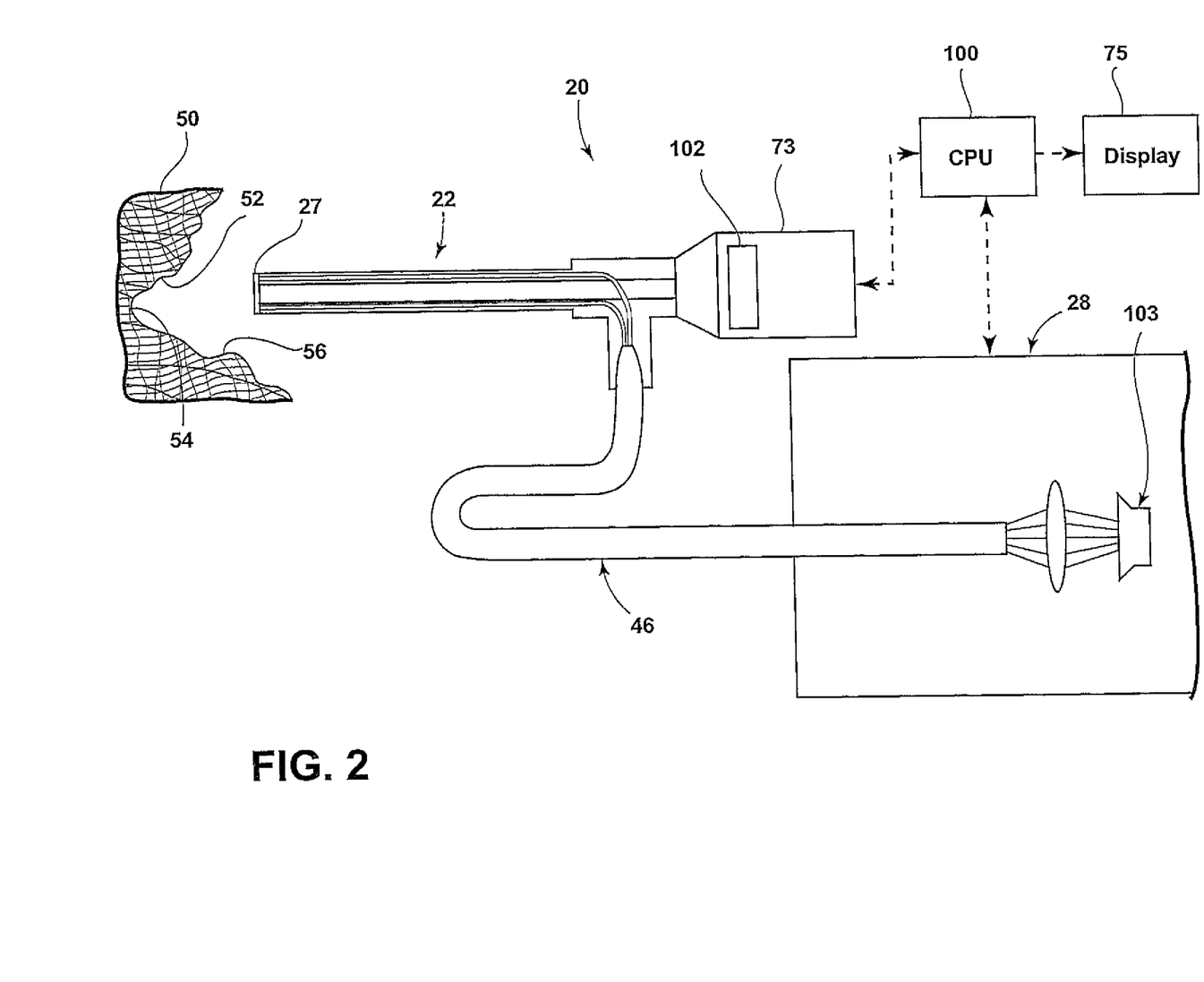
FIG. 2 is a schematic view of the endoscopic system according to the present invention for obtaining a clear image taken within a body cavity.

As illustrated in FIG. 2, the body cavity 50 can have several areas that are at different distances and angles from the distal end 27 of the endoscope 22. For example, the body cavity 50 can have a near area 56 adjacent the distal end 27 of the endoscope 22, far area 54 at a bottom of the body cavity 50 and a middle area 52 between the near area 56 and the far area 54. If the middle area 52 is properly light and focused upon, the near area 56 can be overexposed (e.g., from the light being too bright) and the far area 54 can be underexposed (e.g., from the light being too dim). Therefore, an image captured by a digital capture sensor 102 within the camera 73 would not properly show all portions of the body cavity 50.

Figure 3:
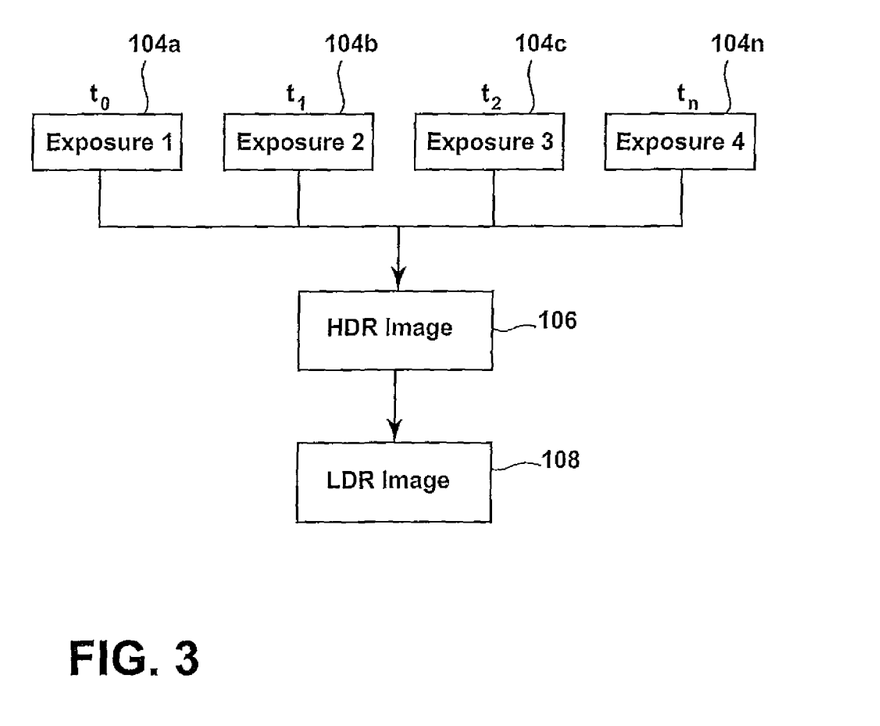
FIG. 3 is a flow chart illustrating a method of obtaining the clear image using the endoscopic system of the present invention.

FIG. 3 illustrates a first method 101 for obtaining a clear image using the endoscopic system 20 of the present invention. In the first method 101 for obtaining a clear image, multiple exposures 104a, 104b, 104c, . . . 104n are taken in sequential order at time $t_0, t_1, t_2, \ldots t_n$, respectively, with the different exposures 104a, 104b, 104c, . . . 104n being in varying degrees of underexposure, normal exposure and overexposure. The normal exposure will obtain a clear view of the middle area 52, the overexposure will obtain a clear view of the far area 54 and the underexposure will obtain a clear view of the near area 56. The variances in exposure can be obtained by varying an intensity of a light source 103 (e.g., LED, xenon or other bulbs) within the light source console 28, by varying an exposure length (e.g., by electronic or mechanical shutter), varying an aperture size, varying a gain and/or other ways well known to those skilled in the art. In the illustrated example, the computer 100 (or other control system) communicates with the light source 103 to vary the intensity of the light source 103 and/or communicates with the camera 73 to vary the exposure length and/or the aperture size. In the illustrated example, underexposure can be accomplished by lowering the intensity of the light source 103, by shortening an exposure length and/or by reducing an aperture size. Likewise, overexposure can be accomplished by increasing the intensity of the light source 103, by lengthening an exposure length and/or by increasing an aperture size.

In the illustrated example, once the series of multiple exposures 104a, 104b, 104c, . . . 104n have been taken, the resulting images are aligned to compensate for differences in position of the endoscope relative to the body cavity 50 during the difference in times $t_0, t_1, t_2, \ldots t_n$ in which the exposures 104a, 104b, 104c, . . . 104n were taken. Properly aligning images is a process well known to those skilled in the art. Once the images have been aligned, a high dynamic range (HDR) image is created at step 106. HDR image creation is well known to those skilled in the art. Tone mapping can then be applied to the HDR image to produce a low dynamic range (LDR) image at step 108. HDR image and LDR image creation can be performed with the computer 100 (or other control system) and the HDR image and/or the LDR image can be viewed on the display screen 75 (or any display device communicating with the computer 100 (or other control system).

Figure 4:
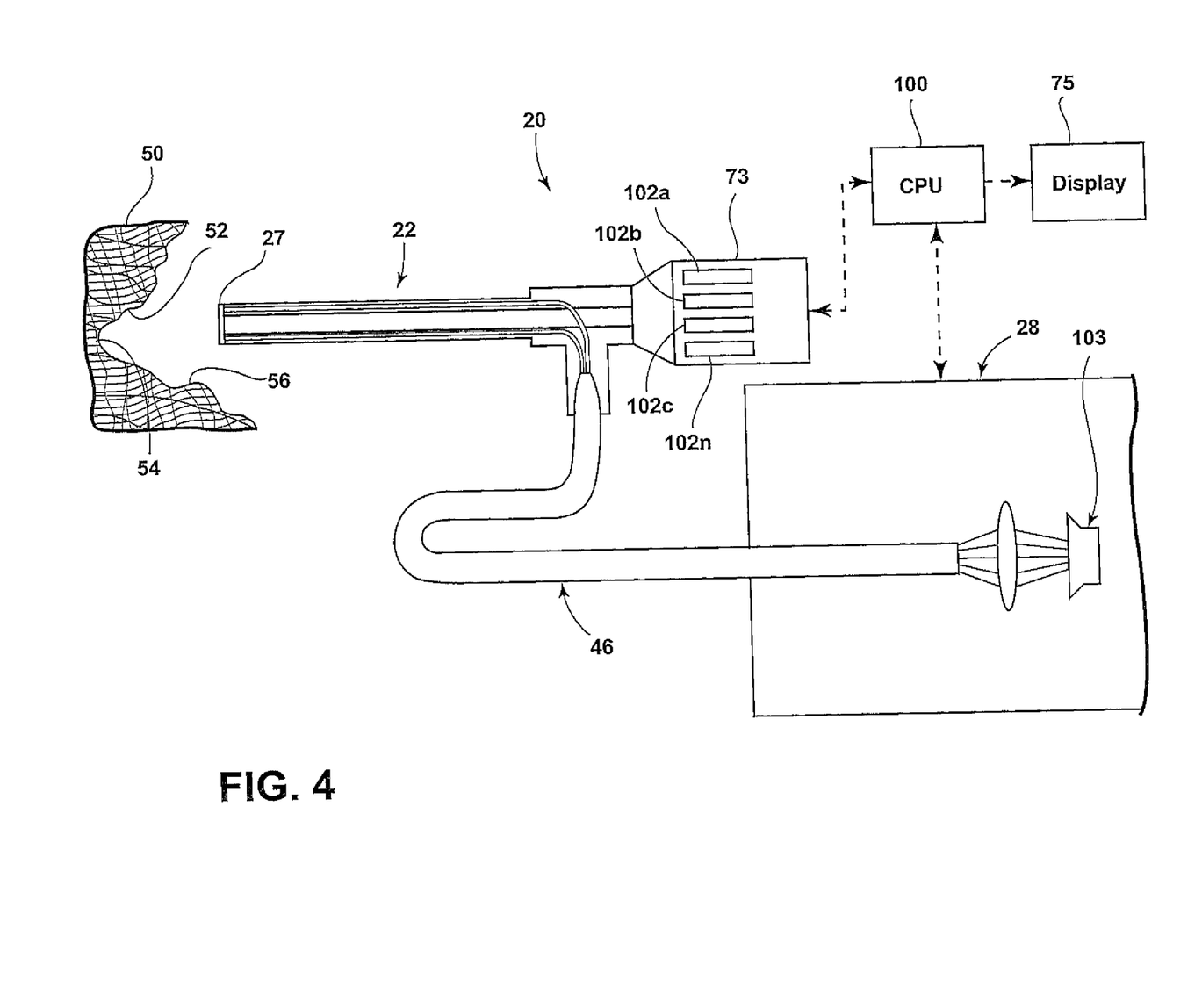
FIG. 4 is a schematic view of a second endoscopic system according to the present invention for obtaining the clear image taken within a body cavity.
Figure 5:
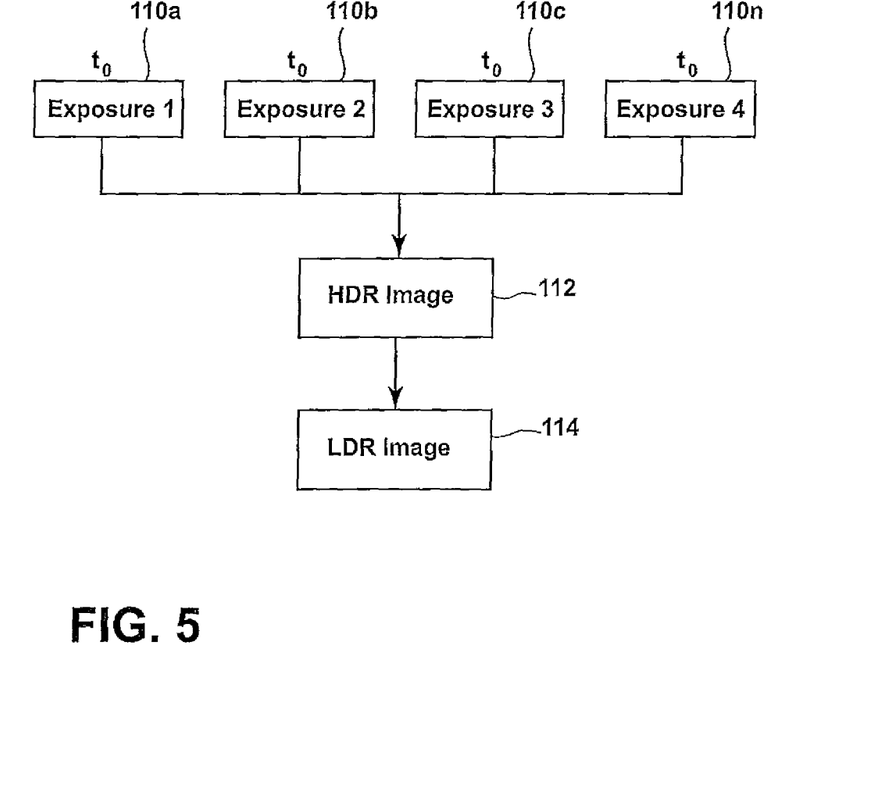
FIG. 5 is a flow chart illustrating a method of obtaining the clear image using the second endoscopic system of the present invention.

FIG. 4 illustrates the endoscopic system 20 for use in a second method 109 (see FIG. 5) for obtaining a clear image using the endoscopic system 20 of the present invention. The endoscopic system 20 illustrated in FIG. 4 is identical to the endoscopic system 20 illustrated in FIG. 2, except that the camera 73' includes a plurality of digital capture sensors 102a, 102b, 102c . . . 102n. FIG. 5 illustrates the second method 109 for obtaining a clear image using the endoscopic system 20 of the present invention having the camera 73' with the plurality of digital capture sensors 102a, 102b, 102c . . . 102n. In the first method 109 for obtaining a clear image, multiple exposures 110a, 110b, 110c, . . . 110n are taken all at the same time $t_0$, with each one of the digital capture sensors 102a, 102b, 102c . . . 102n taking one of the exposures 110a, 110b, 110c, . . . 110n, respectively. All of the exposures 110a, 110b, 110c, . . . 110n will have the same light intensity, such that only the normal exposures, underexposures and overexposures are accomplished by varying an exposure length (e.g., by electronic or mechanical shutter), varying an aperture size, varying a gain and/or other ways well known to those skilled in the art. In the illustrated example, the computer 100 (or other control system) communicates with the camera 73' to vary the exposure length and/or the aperture size. In the illustrated example, underexposure can be accomplished by shortening an exposure length and/or by reducing an aperture size. Likewise, overexposure can be accomplished by lengthening an exposure length and/or by increasing an aperture size. It is contemplated that the endoscopic system 20 could employ a beamsplitter for sending the light to the plurality of digital capture sensors 102a, 102b, 102c . . . 102n.

In the illustrated example, once the multiple exposures 110a, 110b, 110c, . . . 110n have been taken, a high dynamic range (HDR) image is created at step 112 from the multiple exposures 110a, 110b, 110c, . . . 110n. HDR image creation is well known to those skilled in the art. Tone mapping can then be applied to the HDR image to produce a low dynamic range (LDR) image at step 114. HDR image and LDR image creation can be performed with the computer 100 (or other control system) and the HDR image and/or the LDR image can be viewed on the display screen 75 (or any display device communicating with the computer 100 (or other control system).

Figure 6:
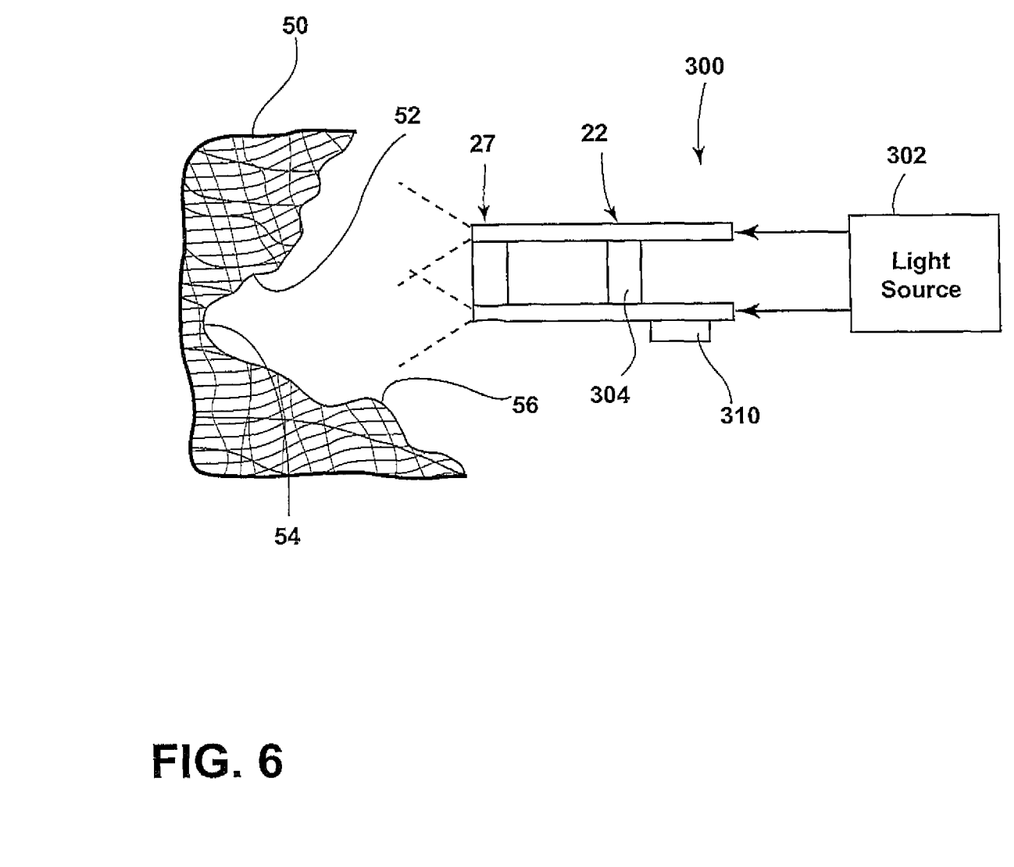
FIG. 6 is a schematic view of a third endoscopic system according to the present invention for obtaining the clear image taken within a body cavity.

FIG. 6 illustrates a third endoscopic system 300 for obtaining a clear image. The third endoscopic system 300 includes the endoscope 22 being supplied with light from a light source 302. The light source 302 could be located within the endoscope 22 or could be supplied to the endoscope 22 via the transmission cable 46 and the light source console 28 as outlined above. The light exits the distal end 27 of the endoscope 22 to impinge upon the middle area 52, the far area 54 and the near area 56 of the body cavity 50. The third endoscopic system 300 also includes an image sensor 304 for capturing images. The image sensor 304 receives control signals from a sensor control 306 and outputs sensor data 308 including the captured images (see FIG. 7). The image sensor 304 could be a charge-coupled device (CCD) image sensor or a complementary metal-oxide-semiconductor (CMOS) sensor. The endoscope 22 can also include a motion sensing device 310 (e.g., accelerometer or inertial motion device) for sensing motion of the endoscope 22.

Figure 7:
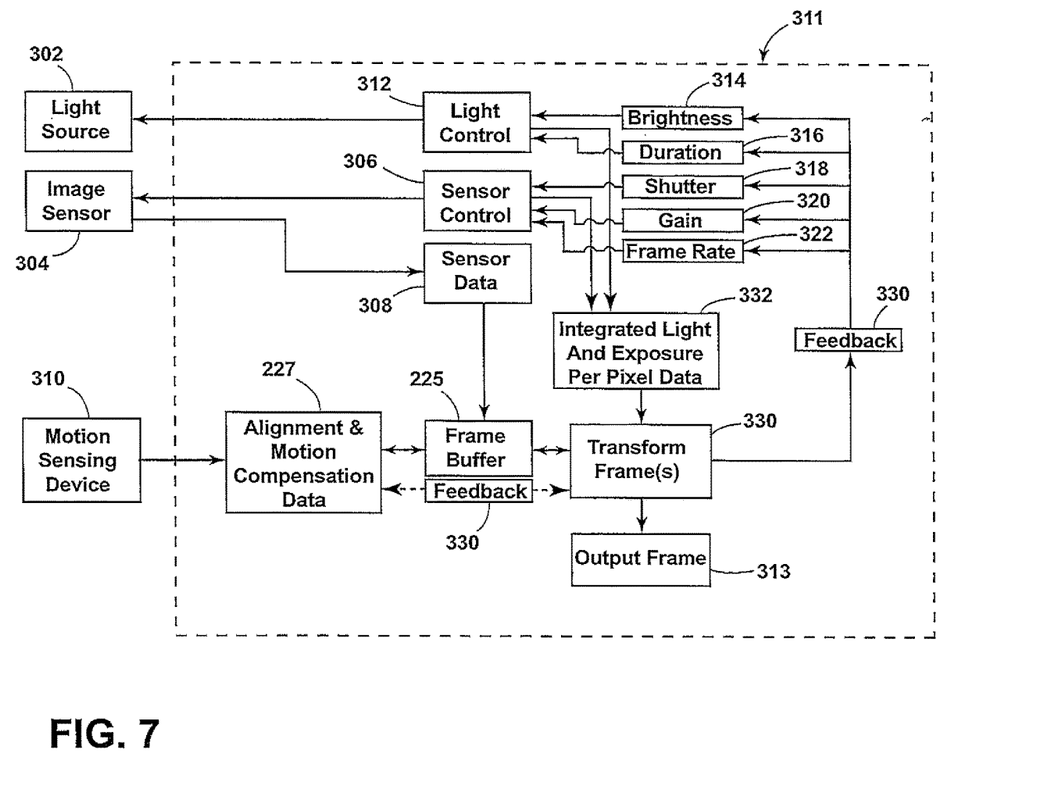
FIG. 7 is a schematic view illustrating a control system of the third endoscopic system according to the present invention.

FIG. 7 illustrates a control system 311 of the third endoscopic system 300 according to the present invention. The control system 311 of the third endoscopic system 300 according to the present invention captures a plurality of frames taken in sequential order (similar to the method 101 as outlined in FIG. 3 above). The frames have different exposures to create a single output frame 313. The control system 311 controls the light source 302 and the image sensor 304 to obtain the frames with different exposures.

The illustrated light source 302 of the third endoscopic system 300 is controlled by a light control 312 of the control system 311 to selectively statically or dynamically alter the intensity (brightness) and/or pulse width modulation (duration) of the light source 302. The light control 312 receives an intensity (brightness) control signal 314 and/or a pulse width modulation (duration) control signal 316 for altering the intensity (brightness) and/or the pulse width modulation (duration) of the light source 302, respectively. The intensity (brightness) control signal 314 instructs the light source 302 to increase or decrease intensity and the pulse width modulation (duration) control signal 316 instructs the light source 302 to alter the duration of the peak intensity of light at a desired intensity level. It is contemplated that the light source 302 could include a mechanical or electrical shuttering mechanism to control the pulse width modulation (duration) of the light source 302.

In the illustrated example, the image sensor 304 of the third endoscopic system 300 is controlled by a sensor control 306 of the control system 311 to capture a desired frame or image. The sensor control 306 receives a shutter (e.g., mechanical (e.g., rolling) or electric) control signal 318, a gain (e.g., electric) control signal 320 and frame rate control signal 322 for controlling the image sensor 304 to obtain different exposures of the frame or image. The shutter control signal 318 instructs the sensor control 306 to control the shutter speed of the image sensor 304. The gain control signal 320 instructs the sensor control 306 to increase or decrease the gain of the image sensor 304. The frame rate control signal 322 instructs the sensor control 306 to increase or decrease the frame rate of the image sensor 304.

The control system 311 of the third endoscopic system 300 creates a clear image by obtaining several frames from the image sensor 304. The control system 311 receives sensor (image or video) data 308 from the image sensor 304 comprising multiple frames of different exposures into a single output frame with high dynamic range. The exposures of the multiple frames can be different because the frames have any of the following differences between the frames: different intensity of light, different duration of light, different shutter speed, different gain and/or different frame rate. In the illustrated example, the frames can be buffered in a frame buffer 225 using alignment and motion compensation data 227 to adjust for motion detected in the frame (e.g., by using edge detection or re-alignement detection algorithms well known to those skilled in the art) and/or to adjust for motion of the image sensor 304 relative to the body cavity 50 sensed by the motion sensing device 310. The frames or images can also be transformed 330 using integrated light and exposure per pixel data 332 from the light control 312 and the sensor control 306 (along with using the alignment and motion compensation data 227 and the frame buffer 225) to maximize the amount of information provided to form the clear image using HDR techniques without introducing distortion or unrealistic effects into the output frame 313. It is also contemplated that the light control 312 along with the transformed 330 frame and the alignment and motion compensation data 227 could be improved using feedback 333.

In the illustrated example, the output frame 313 is therefore created by controlling both the light control 312 and the sensor control 306 along with using the sensor data 308, the alignment and motion compensation data 227 and the integrated light and exposure per pixel data 332 to obtain the clear image. With the ability to control the light source 302, the characteristics of the image sensor 304 including the time duration imposed by the frame rate, the gain and/or the shutter speed are no longer limiting on the exposures of the frames.

Figure 8:
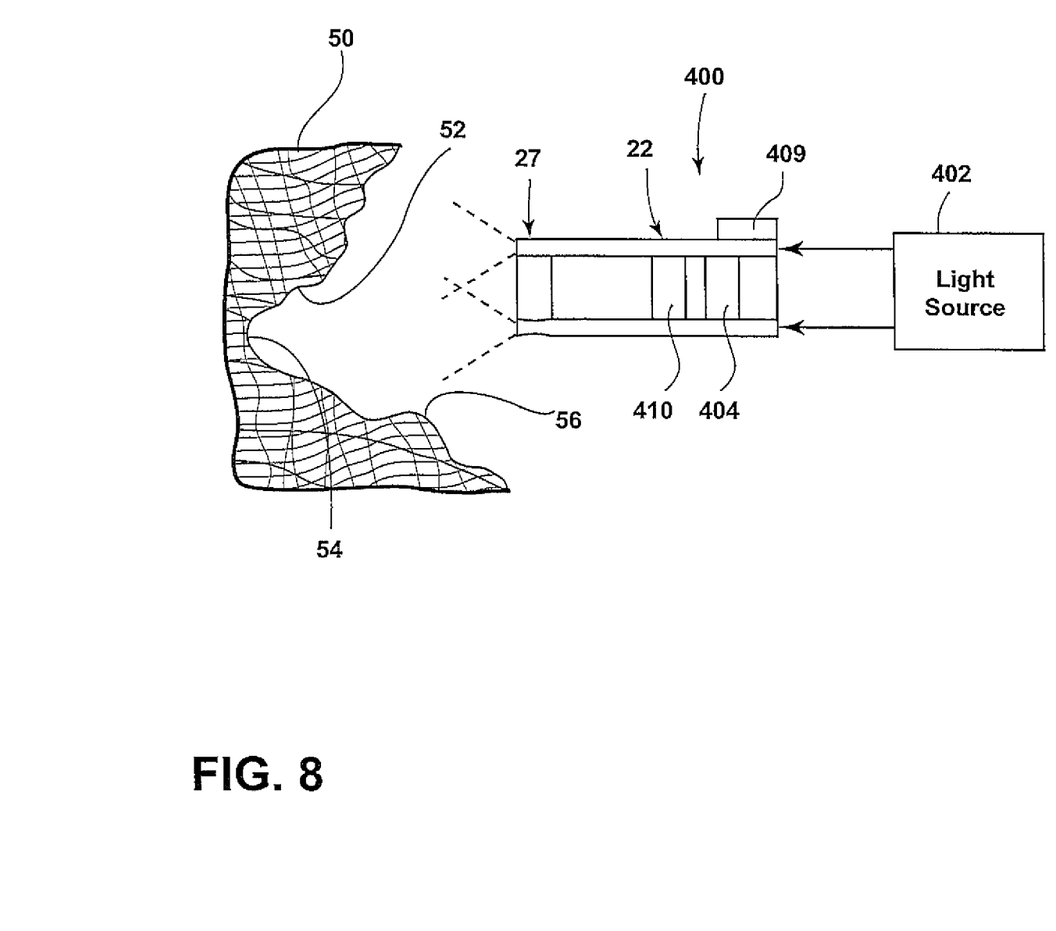
FIG. 8 is a schematic view of a fourth endoscopic system according to the present invention for obtaining the clear image taken within a body cavity.

FIG. 8 illustrates a fourth endoscopic system 400 for obtaining a clear image. The fourth endoscopic system 400 includes the endoscope 22 being supplied with light from a light source 402. The light source 402 could be located within the endoscope 22 or could be supplied to the endoscope 22 via the transmission cable 46 and the light source console 28 as outlined above. The light exits the distal end 27 of the endoscope 22 to impinge upon the middle area 52, the far area 54 and the near area 56 of the body cavity 50. The fourth endoscopic system 400 also includes an image sensor 404 for capturing images. The image sensor 404 receives control signals from a sensor control 406 and outputs image data 408 including the captured images (see FIG. 9). The image sensor 404 could be a charge-coupled device (CCD) image sensor or a complementary metal-oxide-semiconductor (CMOS) sensor. The endoscope 22 also includes a variable-attenuator element device 410 located between the image sensor 404 and the distal end 27 of the endoscope 22 (e.g., directly in front of the image sensor 404 or spaced from the image sensor 404). If the variable-attenuator element device 410 is spaced from the image sensor 404, it is contemplated that imaging optics could be used to align elements of the variable-attenuator element device 410 with pixels of the image sensor 404. Each element of the variable-attenuator element device 410 allows a selected amount of light therethrough. It is contemplated that the variable-attenuator element device 410 could be a liquid crystal display or any other device that includes a matrix of variable-attenuator elements that have a one to one mapping with pixels of the image sensor 404 or one to a group or block of pixels of the image sensor 404.

Figure 9:
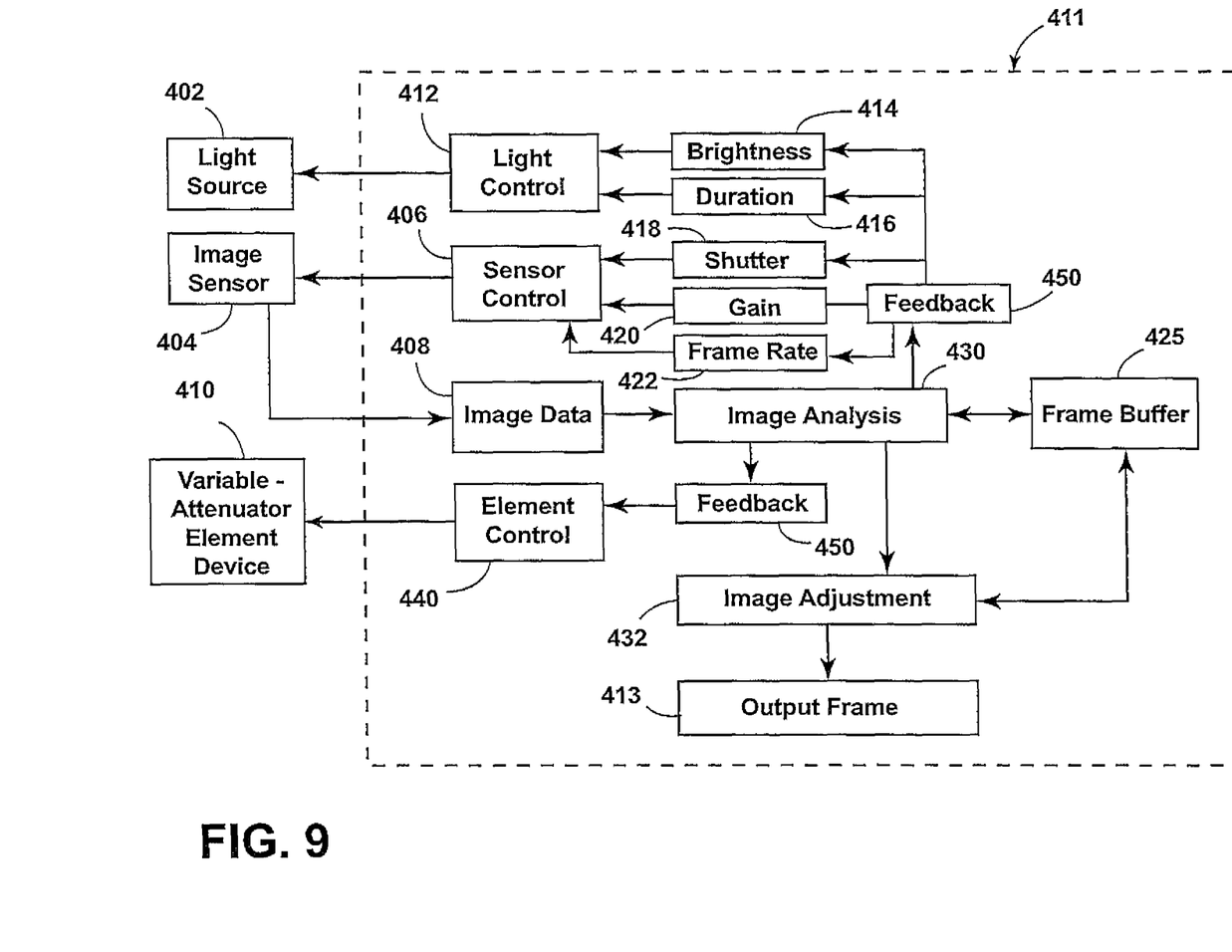
FIG. 9 is a schematic view illustrating a control system of the fourth endoscopic system according to the present invention.

FIG. 9 illustrates a control system 411 of the fourth endoscopic system 400 according to the present invention. The control system 411 of the fourth endoscopic system 400 according to the present invention captures a single frame at a time, with each frame having a clear image. The individual frame will have different exposure areas to create a single clear output frame 413. The control system 411 controls the light source 402 and the image sensor 404 to obtain the frame.

The illustrated light source 402 of the fourth endoscopic system 400 is controlled by a light control 412 of the control system 411 to selectively statically or dynamically alter the intensity (brightness) and/or pulse width modulation (duration) of the light source 402. The light control 412 receives an intensity (brightness) control signal 414 and/or a pulse width modulation (duration) control signal 416 for altering the intensity (brightness) and/or the pulse width modulation (duration) of the light source 402, respectively. The intensity (brightness) control signal 414 instructs the light source 402 to increase or decrease intensity and the pulse width modulation (duration) control signal 416 instructs the light source 402 to alter the duration of the peak intensity of light at a desired intensity level. It is contemplated that the light source 402 could include a mechanical or electrical shuttering mechanism to control the pulse width modulation (duration) of the light source 402.

In the illustrated example, the image sensor 404 of the fourth endoscopic system 400 is controlled by the sensor control 406 of the control system 411 to capture a desired frame or image. The sensor control 406 receives a shutter (e.g., mechanical (e.g., rolling) or electric) control signal 418, a gain (e.g., electric) control signal 420 and frame rate control signal 422 for controlling the image sensor 404 to obtain a desired exposure for the frame or image. The shutter control signal 418 instructs the sensor control 406 to control the shutter speed of the image sensor 404. The gain control signal 420 instructs the sensor control 406 to increase or decrease the gain of the image sensor 404. The frame rate control signal 422 instructs the sensor control 406 to increase or decrease the frame rate of the image sensor 404.

The control system 411 of the fourth endoscopic system 400 creates a clear image by controlling the elements of the variable-attenuator element device 410 in order to maximize a brightness of the darkest portions of the body cavity 50 (e.g., those from the far area 54) while also eliminating or reducing the glare in the brighter portions of the body cavity (e.g., those from the near area 56). The control system 411 uses information in image data 408 from the image sensor 404 (e.g., brightness of the pixel) along with the current attenuation at each pixel of the image sensor 404 from the elements of the variable-attenuator element device 410 (in the image analysis 430) to control the light control 412 and the sensor control 406 via the intensity (brightness) control signal 414, the pulse width modulation (duration) control signal 416, the shutter control signal 418, the gain control signal 420 and/or frame rate control signal 422 along with adjusting the elements of the variable-attenuator element device 410 continuous on a frame by frame basis for image adjustment 432. The frame can be buffered in a frame buffer 425 communicating between the image analysis 430 and the image adjustment 432 using alignment and motion compensation data to adjust for motion detected in the frame (e.g., by using edge detection or re-alignment detection algorithms well known to those skilled in the art) and/or to adjust for motion of the image sensor 404 relative to the body cavity 50 sensed by a motion sensing device 409 (see FIG. 8).

In the illustrated example, the output frame 413 is therefore created by controlling the light control 412, the sensor control 406 along elements of the variable-attenuator element device 410 such that each pixel of the image sensor 404 receives a desired amount of light in order to have a clear image. Therefore, multiple pixels in the image sensor 404 will receive different levels of light. It is contemplated that the image sensor 404 could have certain rows or columns of pixels dedicated to calibrating the elements of the variable-attenuator element device 410. It is also contemplated that the light control 412, the sensor control 406 and an element control 440 that controls the variable-attenuator element device 410 could be improved using feedback 450.

Although the present invention has been described with reference to specific exemplary embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense. For example, the foregoing has involved surgical procedures specific to humans. It will be appreciated that the systems and methods described herein may also be applied to veterinary applications and non-biological applications, for example for inspection of fluid chambers in industrial plants and transport devices. Moreover, it is contemplated that the light source 103, 302, 402 can be located within the endoscope 22 instead of within a light source console 28 separate from the light source 103, 302, 402 with the control system actively controlling the light source 103, 302, 402 within the endoscope 22. Moreover, it is contemplated that any of the first, second and third endoscopic devices could additionally use the variable-attenuator element device 410. Although particular preferred embodiments of the invention have been disclosed in detail for illustrative purposes, it will be recognized that variations or modifications of the disclosed apparatus, including the rearrangement of parts, lie within the scope of the present invention.

What is claimed is:

1. A method of obtaining a clear endoscopic image comprising:
   providing an endoscope;
   providing a light source for the endoscope;
   providing at least one image sensor for capturing a plurality of images of a body cavity;
   emitting light from the endoscope into the body cavity;
   reflecting the light off of a plurality of locations in the body cavity;
   capturing the plurality of images of the light with the at least one image sensor;
   controlling both the light source and the at least one image sensor to vary parameters of the light source and the at least one image sensor such that the plurality of images have underexposed and overexposed regions; and
   combining the plurality of images to result in the clear endoscopic image.

2. The method of obtaining the clear endoscopic image of claim 1, wherein:
   providing at least one image sensor comprises providing a plurality of image sensors; and
   capturing the plurality of images occur simultaneously.

3. The method of obtaining the clear endoscopic image of claim 2, wherein:
   controlling both the light source and the plurality of image sensors comprises varying an exposure length, aperture size and/or gain of each of the plurality of image sensors.

4. The method of obtaining the clear endoscopic image of claim 1, wherein:
   providing at least one image sensor comprises providing a single image sensor; and
   capturing the plurality of images occur sequentially.

5. The method of obtaining the clear endoscopic image of claim 4, wherein:
   controlling both the light source and the single image sensor comprises sequentially varying an exposure length, aperture size and/or gain of the single image sensor during the capturing of the plurality of images sequentially.

6. The method of obtaining the clear endoscopic image of claim 5, wherein:
   controlling both the light source and the single image sensor comprises sequentially varying an intensity and/or pulse width modulation of the light source during the capturing of the plurality of images sequentially.

7. The method of obtaining the clear endoscopic image of claim 4, wherein:
   controlling both the light source and the single image sensor comprises sequentially varying an intensity and/or pulse width modulation of the light source during the capturing of the plurality of images sequentially.

8. The method of obtaining the clear endoscopic image of claim 1, further including:
   sensing motion of the endoscope; and
   deriving motion data from the motion of the endoscope; and
   including buffering the plurality of images before combining the plurality of images to result in the clear endoscopic image by using the motion data to compensate for motion of the endoscope.

9. The method of obtaining the clear endoscopic image of claim 1, wherein:
   the endoscope comprises a hollow shaft inserted into the body cavity.

10. The method of obtaining the clear endoscopic image of claim 1, further including:
    spacing the light source from the endoscope; and
    connecting the light source to the endoscope by a transmission cable;
    wherein light is transmitted from the light source to the endoscope through the transmission cable.

11. The method of obtaining the clear endoscopic image of claim 1, wherein:
    the at least one image sensor and the light source are separate from, but connected to, the endoscope.

12. The method of obtaining the clear endoscopic claim 11, further including:
    directly connecting the at least one image sensor to the endoscope; and connecting the light source to the endoscope by a transmission cable;
wherein light is transmitted from the light source to the endoscope through the transmission cable.

13. An endoscopic system comprising:
an endoscope;
a light source for the endoscope;
at least one image sensor for capturing a plurality of images of a body cavity;
the light source being configured to emit light from the endoscope and into the body cavity such that the light is reflected off of a plurality of locations in the body cavity; and
a control system for controlling both the light source and the at least one image sensor to vary parameters of the light source and the at least one image sensor such that the plurality of images have underexposed and overexposed regions.

14. The endoscopic system of claim 13, wherein:
the at least one image sensor comprises a plurality of image sensors configured to simultaneously capture the plurality of images.

15. The endoscopic system of claim 14, wherein:
the control system controls both the light source and the plurality of image sensors by varying an exposure length, aperture size and/or gain of each of the plurality of image sensors.

16. The endoscopic system of claim 13, wherein:
the at least one image sensor comprises a single image sensor configured to sequentially capture the plurality of images.

17. The endoscopic system of claim 16, wherein:
the control system controls both the light source and the single image sensor by sequentially varying an exposure length, aperture size and/or gain of the single image sensor during capturing of the plurality of images.

18. The endoscopic system of claim 17, wherein:
the control system controls both the light source and the single image sensor by sequentially varying an intensity and/or pulse width modulation of the light source during capture of the plurality of images sequentially.

19. The endoscopic system of claim 16, wherein:
the control system controls both the light source and the single image sensor by sequentially varying an intensity and/or pulse width modulation of the light source during capture of the plurality of images sequentially.

20. The endoscopic system of claim 13, further including:
a motion sensor for sensing motion of the endoscope, the motion sensor outputting sensor data for buffering the plurality of images before combining the plurality of images to result in a clear endoscopic image.

21. The endoscopic system of claim 13, wherein:
the endoscope comprises a hollow shaft for insertion into the body cavity.

22. The endoscopic system of claim 13, wherein:
the light source is spaced from the endoscope;
a transmission cable connects the light source to the endoscope; and
light is transmitted from the light source to the endoscope through the transmission cable.

23. The endoscopic system of claim 13, wherein:
the at least one image sensor and the light source are separate from, but connected to, the endoscope.

24. The endoscopic system of claim 23, wherein:
the at least one image sensor is directly connected to the endoscope;
a transmission cable connects the light source to the endoscope; and
light is transmitted from the light source to the endoscope through the transmission cable.

* * * * *